(12) United States Patent
Heikenfeld

(10) Patent No.: US 11,317,835 B2
(45) Date of Patent: May 3, 2022

(54) SWEAT SENSING WITH ANALYTICAL ASSURANCE

(71) Applicant: University Of Cincinnati, Cincinnati, OH (US)

(72) Inventor: Jason Charles Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 519 days.

(21) Appl. No.: 16/172,188

(22) Filed: Oct. 26, 2018

(65) Prior Publication Data

US 2019/0059795 A1 Feb. 28, 2019

Related U.S. Application Data

(63) Continuation of application No. 15/512,982, filed on Mar. 21, 2017, now abandoned.

(60) Provisional application No. 62/155,527, filed on May 1, 2015, provisional application No. 62/053,388, filed on Sep. 22, 2014.

(51) Int. Cl.
*A61B 5/145* (2006.01)
*A61B 5/00* (2006.01)
*A61B 5/1495* (2006.01)

(52) U.S. Cl.
CPC ........ *A61B 5/14517* (2013.01); *A61B 5/1495* (2013.01); *A61B 5/4266* (2013.01); *A61B 5/6801* (2013.01); *A61B 5/6832* (2013.01); *A61B 2560/0223* (2013.01)

(58) Field of Classification Search
None
See application file for complete search history.

(56) References Cited

U.S. PATENT DOCUMENTS 4,190,060 A 2/1980 Greenleaf et al.
4,542,751 A 9/1985 Webster et al.
(Continued)

FOREIGN PATENT DOCUMENTS

CA 2869469 A1 10/2013
CN 101489470 A 7/2009
(Continued)

OTHER PUBLICATIONS

International Searching Authority, Search Report and Written Opinion issued in International Application No. PCT/US2017/067495 dated Mar. 1, 2018, 10 pages.
(Continued)

*Primary Examiner* — Michael R Bloch
(74) *Attorney, Agent, or Firm* — Wood Herron & Evans LLP

(57) ABSTRACT

A sweat sensor device (200) with analytical assurance includes at least one sensor (220) for detecting a first analyte, and at least one calibration medium (270) containing at least the first analyte. When the first analyte in the at least one calibration medium (270) comes into contact with the at least one sensor (220), the calibration medium (270) provides a calibration of the at least one sensor (220). A sweat sensor device (200) may further include a carrier (240) having at least one aperture (220*a*) and a reservoir (254) for storing the at least one calibration medium (270). The at least one aperture (220*a*) provides fluidic access to the at least one sensor (220) from the reservoir (254).

9 Claims, 6 Drawing Sheets

(56) References Cited

U.S. PATENT DOCUMENTS

| | | | |
|---|---|---|---|
| 4,756,314 A | 7/1988 | Eckenhoff et al. | |
| 4,820,263 A | 4/1989 | Spevak et al. | |
| 5,036,861 A | 8/1991 | Sembrowich et al. | |
| 5,050,604 A | 9/1991 | Reshef et al. | |
| 5,064,618 A * | 11/1991 | Baker | G01N 33/48707 422/82.01 |
| 5,140,985 A | 8/1992 | Schroeder et al. | |
| 5,246,003 A | 9/1993 | DeLonzor | |
| 5,293,770 A * | 3/1994 | Hansen | G01N 27/4163 204/401 |
| 5,438,984 A | 8/1995 | Schoendorfer | |
| 5,443,077 A * | 8/1995 | Krogh | A61B 5/14539 128/897 |
| 5,556,789 A | 9/1996 | Goerlach-Graw et al. | |
| 5,814,599 A | 9/1998 | Mitragotri et al. | |
| 5,944,662 A | 8/1999 | Schoendorfer | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kumik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2005/0277912 A1 * | 12/2005 | John | G16H 20/17 604/890.1 |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0179403 A1 | 7/2010 | Martinsen et al. | |
| 2010/0198521 A1 | 8/2010 | Haick | |
| 2010/0234712 A1 | 9/2010 | Sugenoya et al. | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 * | 11/2011 | Yamashita | A61B 5/14521 600/345 |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0245388 A1 | 9/2013 | Rafferty et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |

FOREIGN PATENT DOCUMENTS

| | | |
|---|---|---|
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |

(56) References Cited

FOREIGN PATENT DOCUMENTS

| WO | 2016130905 A1 | 8/2016 |
|---|---|---|
| WO | 2016138087 A1 | 9/2016 |
| WO | 2017019602 A1 | 2/2017 |

OTHER PUBLICATIONS

International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Search Report and Written Opinion issued in International Application No. PCT/US2014/061083 dated Mar. 31, 2015, 18 pages.
International Searching Authority, Search Report and Written Opinion issued in International Application No. PCT/US2015/032830 dated Aug. 14, 2015, 9 pages.
International Searching Authority, Search Report and Written Opinion issued in International Application No. PCT/US2015/032843 dated Oct. 26, 2015, 11 pages.
International Searching Authority, Search Report and Written Opinion issued in International Application No. PCT/US2015/032866 dated Nov. 19, 2015, 12 pages.
International Searching Authority, Search Report and Written Opinion issued in International Application No. PCT/US2015/032893 dated Nov. 13, 2015, 14 pages.
International Searching Authority, Search Report and Written Opinion issued in International Application No. PCT/US2015/040113 dated Feb. 4, 2016, 13 pages.
International Searching Authority, Search Report and Written Opinion issued in International Application No. PCT/US2015/051439 dated Dec. 28, 2015, 7 pages.
International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.
International Searching Authority, Search Report and Written Opinion issued in International Application No. PCT/US16/18635 dated May 6, 2016, 12 pages.
International Searching Authority, Search Report and Written Opinion issued in International Application No. PCT/US16/17726 dated May 12, 2016, 9 pages.
International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.
Fu et al., "Controlled Reagent Transport in Disposable 2D Paper Networks", The Royal Society of Chemistry 2010, Lab Chip, 2010, 10, 918-920.
European Patent Office, Written Opinion of the International Search Authority / International Preliminary Report on Patentability for PCT/US2013/035092 dated Oct. 16, 2014 (14 pages).
Australian Patent Office, Patent Examination Report No. 1 issued in Australian Application No. 2013243541 dated Nov. 25, 2016, 4 pages.
European Patent Office, Partial European Search Report issued in European Application No. 16203346.8-1657 dated Mar. 24, 2017, 7 pages.
International Searching Authority, Search Report and Written Opinion issued in International Application No. PCT/US16/59392 dated Oct. 28, 2016, 13 pages.
International Searching Authority, Search Report and Written Opinion issued in International Application No. PCT/US16/50928 dated Sep. 9, 2016, 8 pages.
Japanese Patent Office, Office Action issued in Japanese Application No. 2015-504702 dated Jan. 20, 2017, 7 pages (including English language translation).
Stoppa, Matteo, et. al., "Wearable Electronics and Smart Tectiles: A Critical Review," Sensors, 2014, pp. 11957-11992, vol. 14 (36 pages).
International Searching Authority, Search Report and Written Opinion issued in International Application No. PCT/US16/43862 dated Oct. 19, 2016, 14 pages.
International Searching Authority, Search Report and Written Opinion issued in International Application No. PCT/US2017/013453 dated May 18, 2017, 14 pages.
International Searching Authority, Search Report and Written Opinion issued in International Application No. PCT/US2017/039421 dated Sep. 6, 2017, 10 pages.
International Searching Authority, Search Report and Written Opinion issued in International Application No. PCT/US2017/040588 dated Sep. 25, 2017, 11 pages.
Chinese Patent Office, First Office Action issued in Chinese Application No. 201380028053.8 dated Dec. 21, 2105, 4 pages.
Australian Patent Office, Notice of Acceptance for Patent Applicatin issued in Australian Application No. 2013243541 dated Mar. 23, 2017 (3 pages).
Chinese Patent Office, Second Office Action issued in Chinese Application No. 201380028053.8 dated Sep. 20, 2016, 8 pages (including English language translation).
Chinese Patent Office, Third Office Action issued in Chinese Application No. 201380028053.8 dated Mar. 20, 2017, 17 pages (including English language translation).
European Patent Office, Supplemental European Search Report issued in European Application No. 15799514.3-1657 dated Dec. 7, 2017, 8 pages.
European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.

(56) References Cited

OTHER PUBLICATIONS

Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.

International Searching Authority, Search Report and Written Openin in International Application No. PCT/US2016/043862, dated Oct. 19, 2016 (14 pages).

European Patent Office, Official Communication for EP Application No. 13 718 933.8-1101 dated Feb. 14, 2018 (5 pages).

European Patent Office, Extended European Search Report issued in European Application No. 15819306.0-1115 dated Feb. 9, 2018 (9 pages).

European Patent Office, Extended Search Report issued for European Application No. 15800043.0-1115 dated Apr. 16, 2018, 11 pages.

\* cited by examiner

SWEAT SENSING WITH ANALYTICAL ASSURANCE

CROSS-REFERENCE TO RELATED APPLICATIONS

This application is a continuation application of U.S. application Ser. No. 15/512,982 filed on Mar. 21, 2017 and claims the benefit of U.S. Provisional Application No. 62/053,388, filed on Sep. 22, 2014, and 62/155,527, filed on May 1, 2015, the disclosures of which are hereby incorporated by reference herein in their entirety.

BACKGROUND OF THE INVENTION

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Small, portable, and wearable biosensors are difficult to make so that they are precise and accurate. Such sensors are often generally challenged in their ability to make quality analytical measurements equal to what can be done with a dedicated measurement machine or large lab. This is especially true for sensors integrated in a small patch or wearable device because of the need for miniaturization and lower cost, and because such devices are placed in less controllable environments than many lab or machine settings.

Many of the drawbacks stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. Further, a sweat sensor capable of analytical assurance is needed. With such a new invention, sweat sensing could become a compelling new paradigm as a biosensing platform.

SUMMARY OF THE INVENTION

The present invention provides a wearable sweat sensor device capable of analytical assurance. In one embodiment, a sweat sensor device with analytical assurance includes at least one sensor for detecting a first analyte, and at least one calibration medium containing at least the first analyte. When the first analyte in the at least one calibration medium comes into contact with the at least one sensor, the concentration medium provides a calibration of the at least one sensor.

In another embodiment, a method of detecting a solute in sweat includes directing a calibration medium in a device to at least one sensor for detecting the solute in the device, calibrating the at least one sensor, positioning the device on skin, directing sweat to the device, and measuring the solute in the sweat using the device.

In another embodiment, a method of detecting a solute in sweat using a device for detecting the solute in sweat, the device including at least one sensor, includes providing fluidic access to the at least one sensor through an aperture in a first backing element, directing at least one calibration medium to the at least one sensor through the aperture, calibrating the at least one sensor, placing the device on skin, directing sweat to the device, and measuring the solute in the sweat using the device.

BRIEF DESCRIPTION OF THE DRAWINGS

The objects and advantages of the present invention will be further appreciated in light of the following detailed descriptions and drawings in which.

DETAILED DESCRIPTION OF THE INVENTION

Figure 1A:
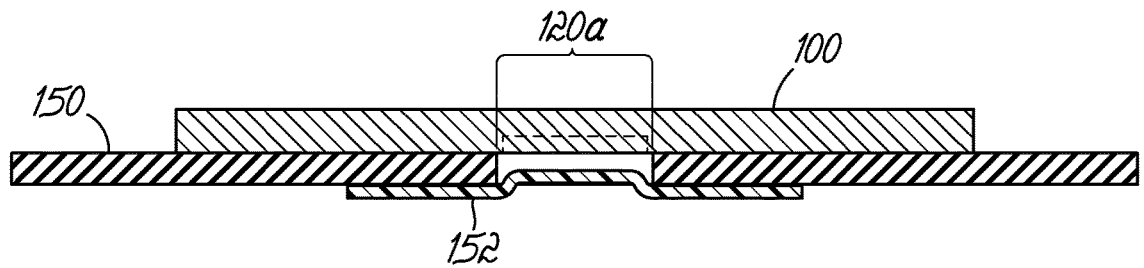
FIG. 1A is a cross-sectional view of a device according to an embodiment of the present invention.

The present application has specification that builds upon International Application Nos. PCT/US13/35092, filed Apr.

2, 2013, PCT/US14/61083, filed Oct. 17, 2014, PCT/US14/61098, filed Oct. 17, 2014, PCT/US15/32830, filed May 28, 2015, PCT/US15/32843, filed May 28, 2015, PCT/US15/32866, filed May 28, 2015, PCT/US15/32893, filed May 28, 2015, and PCT/US15/40113, filed Jul. 13, 2015, the disclosures of which are hereby incorporated herein by reference in their entirety.

Embodiments of the present invention apply at least to any type of sweat sensor device that measures sweat, sweat generation rate, sweat chronological assurance, sweat solutes, solutes that transfer into sweat from skin, properties of or items on the surface of skin, or properties or items beneath the skin. Embodiments of the present invention further apply to sweat sensing devices that have differing forms including: patches, bands, straps, portions of clothing, wearables, or any suitable mechanism that reliably brings sweat stimulating, sweat collecting, and/or sweat sensing technology into intimate proximity with sweat as it is generated by the body. While certain embodiments of the present invention utilize adhesives to hold the device near the skin, other embodiments include devices held by other mechanisms that hold the device secure against the skin, such as a strap or embedding in a helmet.

Sweat stimulation, or sweat activation, can be achieved by known methods. For example, sweat stimulation can be achieved by simple thermal stimulation, by orally administering a drug, by intradermal injection of drugs such as methylcholine or pilocarpine, and by dermal introduction of such drugs using iontophoresis. Sweat can also be controlled or created by asking the subject using the patch to enact or increase activities or conditions which cause them to sweat. These techniques may be referred to as active control of sweat generation rate.

Certain embodiments of the present invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor.

In an aspect of the present invention, a sweat sensor device is capable of providing analytical assurance as described below. Analytical assurance means (but is not limited to) an assurance of the precision, accuracy, or quality of measurements provided by the sweat sensor device. In other words, analytical assurance could further refer to improved confidence in the precision, accuracy, or quality of measurements made.

Figure 1B:
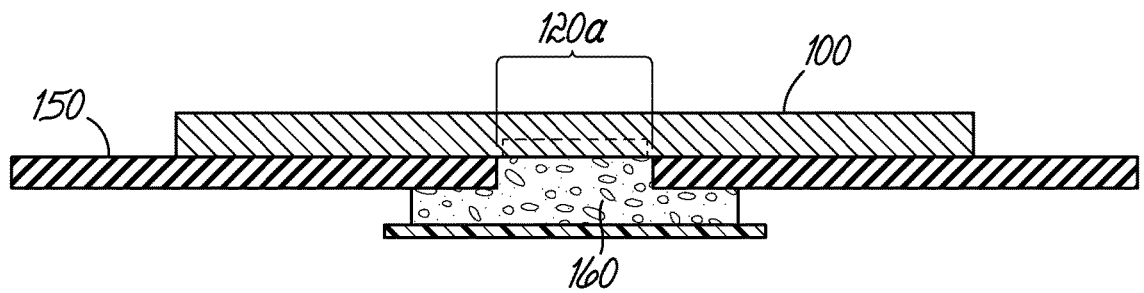
FIG. 1B is a cross-sectional view of the device of FIG. 1A during calibration.
Figure 1C:
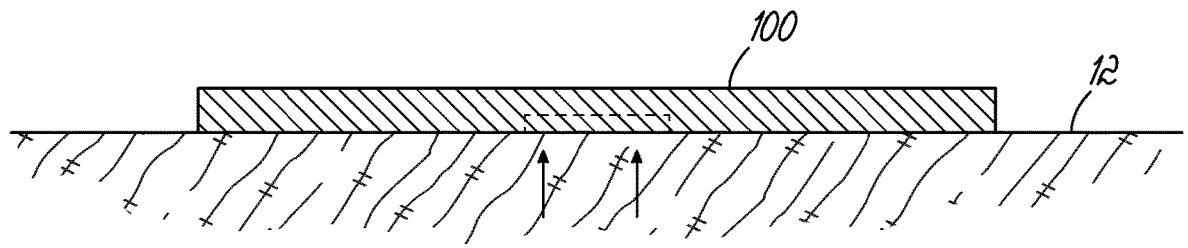
FIG. 1C is a cross-sectional view of the device of FIG. 1A positioned on skin.

With reference to FIGS. 1A-1C, a sweat sensor device is designed to be calibrated before use. The sweat sensor device 100 has an adhesive side supported by carrier 150 and carrier 152. Carriers 150, 152 could be a variety of materials. By way of example, carriers 150, 152 could be wax or siliconized paper, such as that used in bandage backings. Carrier 150 is sufficiently sealed against the underside of the device 100 such that it covers and seals the adhesive side of the device 100 with exception to aperture 120a. Aperture 120a allows access to one or more sensors (not shown) via direct access or through microfluidic connections. Carriers 150, 152 are removable from device 100. In the illustrative embodiment, the carrier 152 may be removed without removing the carrier 150.

With reference to FIG. 1B, the carrier 152 of the device 100 may be removed to expose the aperture 120a. A sponge 160, which is permeated with a calibrating solution or medium, is pressed against the device 100 to bring the solution in contact with the sensors of the device 100. Importantly, the carrier 150 shields the rest of the device 100 from the application of the calibrating solution but allows the calibration solution or medium to contact at least one sensor though the aperture 120a. The calibrating solution is provided with pre-determined concentration of solutes or other properties of sweat (e.g., pH). The sponge 160 is held against the device 100 for a period of time adequate to allow the sensors to be calibrated based on measurements of analytes in the solution. The time required for a sensor to be calibrated may vary depending on the sensor stabilization time. The time required for a sensor to stabilize can be, for example, as short as several minutes, to as long as 30 minutes for a nM or pM sensor, or as long as multiple hours for ion-selective electrodes that require wetting periods. Once the sweat sensor device 100 has completed calibration, it is now capable of providing sweat measurements with analytical assurance. Carrier 150 may be subsequently removed, and the device 100 may be applied to skin 12 to be used, as shown in FIG. 1C. The calibration techniques disclosed herein significantly improve the ease with which sensors in patches or wearable devices may be calibrated. Conventional sensor calibration techniques require the sensor to be dipped into a beaker or vial containing a calibration solution. For a sensor in a patch or wearable device, as taught herein, such techniques are generally impractical for commercial usage (e.g. a non-laboratory setting such as a home, or may damage or degrade the sweat sensor device.

A variety of techniques and compositions may be used to calibrate sensors according to methods of the present invention. For instance, a calibration solution may be used where the solution composition is based on properties of skin, contaminants on skin, or other solutes or properties that would affect analytical assurance for a sensor placed on skin. A collected human sweat sample or an artificial sweat sample (e.g., such as one available from Pickering Laboratories) may also be used to calibrate a sensor. Further, the solution could be concentrated, diluted, or spiked with a solute or property of interest. The selected concentration of solutes could be, for example: low enough to confirm the lower limit of detection for the sensor, or could be near or below physiological levels to confirm the accuracy of the sensor. Where a device includes more than one sensor, the concentration of solutes in the applied sponge 160 could be designed to calibrate all of the sensors, one of the sensors, or a subset of the sensors. In an alternate embodiment, sponge 160 can be replaced by any other technique to apply a calibrating solution, including for example using a spray bottle (not shown).

In one embodiment, more than one calibration solution may be applied with similar or different concentrations or properties of sweat to calibrate a sensor. In the embodiment illustrated in FIG. 1B, more than one sponge 160 may be applied in sequence (not shown) to the device 100. When multiple sponges 160 are applied in sequence, the different sponges 160 may have calibration solutions, for example, that increase in concentration, or properties to calibrate sensor response or linearity with change in concentration. Alternatively, the different sponges 160 may have solution concentrations that increase or decrease to determine the rate of response or adaptation of sensors. Determining the sensor response rate improves analytical assurance because some sensors experience a lag between the change in analyte concentration in solution and the change in measured analyte concentration that is caused by the analytes' tendency to adhere to the sensor.

The application of a calibration solution (e.g., using the sponge 160) also allows one to determine other properties such as drift of sensors over time. In one embodiment, a sponge 160 may be applied for a sufficient time such that sensor drift can be determined to improve the analytical assurance for the sensor. For high quality sensors, drift typically is observable only after a period of hours or more.

Figure 2A:
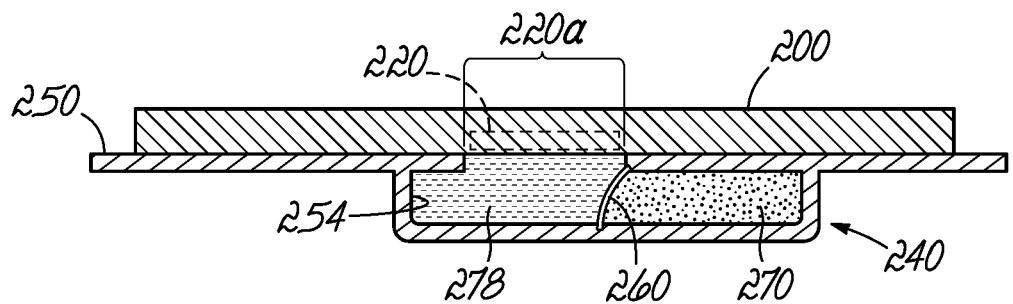
FIG. 2A is a cross-sectional view of a device and a calibration module according to an embodiment of the present invention.
Figure 2B:
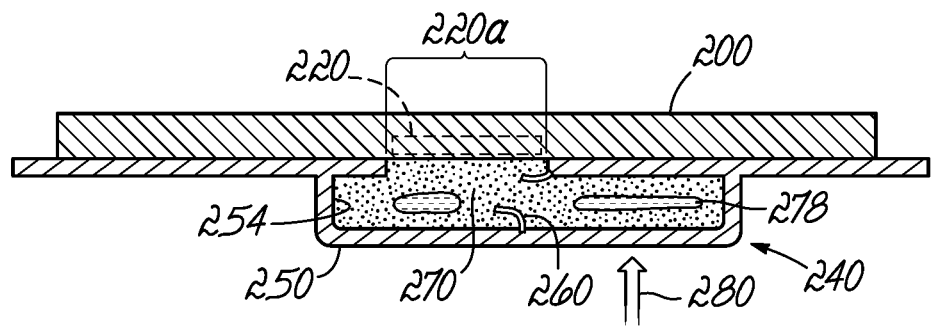
FIG. 2B is a cross-sectional view of the device and calibration module of FIG. 2A during calibration.

With reference to FIGS. 2A and 2B, a sweat sensor device 200 is coupled to a calibration module 240. The calibration module 240 includes a housing 250 that defines a reservoir 254. The calibration module 240 acts as a carrier for the device 200 similar to the carrier 150 of FIG. 1A. Housing 250 includes aperture 220a that provides fluidic access from the reservoir 254 to at least one sensor 220 (shown in FIG. 2C) within the device 200. A calibration solution 270 is sealed inside the housing 250 by a membrane 260. On the other side of the membrane 260 (i.e., the side of the reservoir 254 adjacent the aperture 220a) is a gas, inert gas, or fluid 278. The application of pressure (as indicated by arrow 280) to the housing 250 causes the membrane to rupture, as shown in FIG. 2B. In this regard, the calibration module 240 has been activated by the pressure applied in the direction of arrow 280 and the calibration solution 270 comes into contact with one or more sensors of the device 200 near aperture 220a. The pressure may be applied, for example, by a user pressing against the housing 250. In one embodiment, to ensure the sensors are wetted, the calibration module 240 may include a sponge material (not shown) on the side of the membrane 260 adjacent to the aperture 220a. Alternatively, the housing 250 may be designed such that gravity is not a factor in the movement of the calibration solution 270 past the sensor and/or that a shaking motion could be applied to ensure calibration solution 270 comes into contact with one or more sensors of the device 200.

Figure 2C:
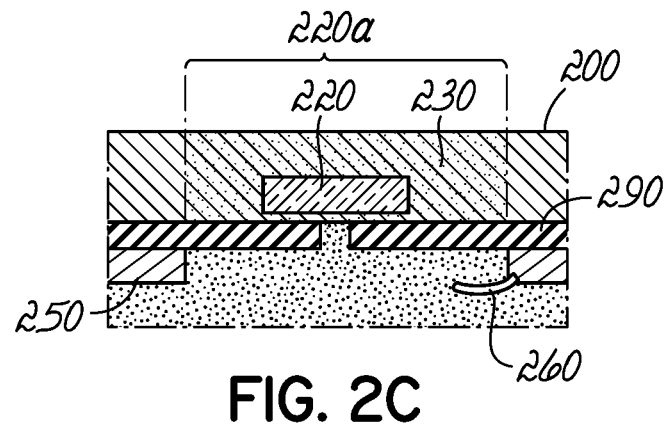
FIG. 2C is a cross-sectional view of a portion of the device of FIG. 2A.

In one embodiment, the device 200 may include a flow restricting element. As illustrated in FIG. 2C, the flow restricting element 290 may be positioned adjacent the aperture 220a between the device 200 and the housing 250. A wicking material 230 surrounds a sensor 220 and the flow restricting element 290. The flow restricting element 290 may be, for example, a flow limiting element (e.g., reduced porosity in a textile), a flow constriction element (e.g., small pore or aperture), or a flow stopping element. In the illustrated embodiment, the restricting element 290 is a polymer film with a flow restriction component, such as a small gap. In this configuration, the gap restricts the flow of sweat from the skin to wicking material 230. The flow restricting element may prevent a sweat pumping element, such as wicking material 230, within the device 200 from being saturated with the calibration solution 270. In other words, the flow restricting element 290 prevents the calibration solution 270 from saturating the sweat pumping capacity of device 200. While the restricting element 290 in FIG. 2C is shown as being part of device 200, other configurations and techniques are capable of being used to restrict the flow of sweat to the device 200. In one embodiment, the flow restricting element 290 could be a component of element 250 shown in FIGS. 2A and 2B. In another embodiment, pumping or wicking elements could be removed or not fluidically connected to sensors during calibration and added or connected after calibration is complete.

With further reference to FIGS. 2A and 2B, in one embodiment, the calibration solution 270 could be a gel and component 278 may be a gel (rather than the gas 278 discussed above). As membrane 260 ruptures, the calibration gel 270 comes in contact with the gel 278. The solutes in the calibration gel 270 will diffuse, rather than flow by advection, through the gel 278 to come into contact with one or more sensors of the device 200 near aperture 220a. The materials for gels 270, 278 could be similar or different gel materials, so long as the diffusion of solutes in gel 270 can occur through the gel 278. This configuration allows for calibration of the sensors over a varying concentration level as the calibration solution diffuses into gel 278. For example, a sensor could be calibrated between a zero concentration level—which is the starting concentration for gel 270—and the maximum concentration of the solutes which results from slow diffusion-based mixing of concentrations between gel 270 and gel 278 where gel 270 contains a concentration of at least one solute to be used for calibration. Although a calibration involving a concentration gradient could be achieved where components 270, 278 are liquids, such a calibration would be less predictable, because fluid mixing is often more chaotic than the diffusion of solutes where components 270, 278 are gels, which are more homogeneous.

With further reference to FIG. 2B, in one embodiment, the rupture of membrane 260 could be caused by removing the housing 250 from the device 200. This may be convenient for use, since the device 200 cannot be adhered onto skin until housing 250 is removed. During the removal of the housing 250, the calibration solution 270 could be quickly (as little as seconds) brought into contact with sensors of the device 200, and the device may be applied to the skin. The calibration of the sensors may continue until sweat from the skin replaces the calibration solution, which is a process that may take at least several minutes, if not much longer. This approach ensures that the user always calibrates the device before use, without any extra steps beyond the expected minimum (i.e., removal of the housing 250) for applying an adhesive patch to the skin. This may be more broadly referred to as calibration which occurs as backing element or material, or housing material, is removed from the adhesive side of a device.

Figure 3:
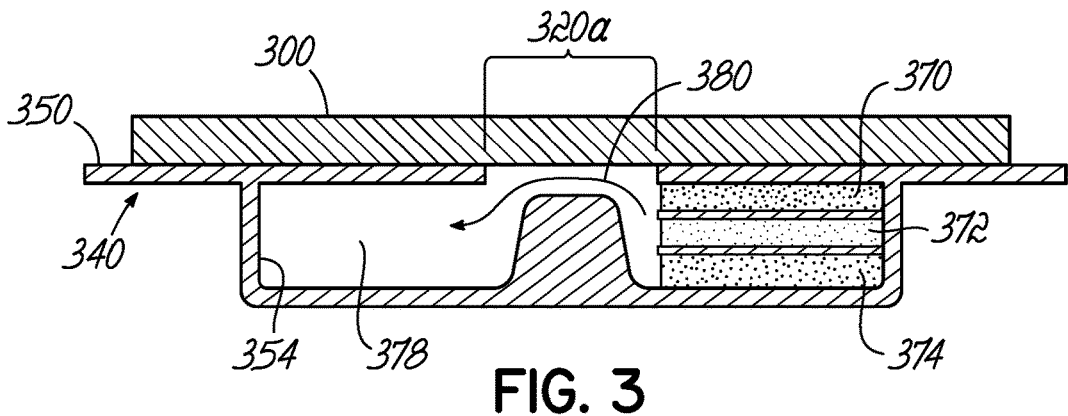
FIG. 3 is a cross-sectional view of a device and a calibration module according to an embodiment of the present invention.

In one aspect of the invention, a calibration module may include more than one calibration solution or medium. With reference to FIG. 3, a device and a calibration module according to another embodiment of the invention are shown. The device 300 and calibration module 340 are similar in construction to those shown in FIGS. 2A and 2B, and similar reference numerals refer to similar features shown and described in connection with FIGS. 2A and 2B, except as otherwise described below. The calibration module 340 includes a housing 350, and includes multiple solutions 370, 372, 374 within the reservoir 354. The solutions 370, 372, 374 could sequentially flow over aperture 320a past the sensors (as indicated by arrow 380) inside calibration module 340. The solutions 370, 372, 374 displace gas 378 as they flow past aperture 320a. The calibration module 340 may include a mechanism for pumping, gating, or introducing fluids as known by those skilled in the art. For example, component 378 could be a sponge material (not shown) that wicks the solutions 370, 372, 374 against the sensor. Further, the device 300 may include an electrowetting gate (not shown) to form a capillary between the solutions 370, 372, 374 and the sponge. It will be recognized that more complex arrangements with mechanical pumps and valves could be also used in other embodiments of the present invention. The solutions 370, 372, 374 may have the same or varying concentrations. In one embodiment, the solutions 370, 372, 374 contain a lowest concentration, a middle concentration, and a highest concentration, respectively, for calibration.

In another aspect of the present invention, a calibration module may include one or more calibration solutions containing more than one solute. Such a configuration allows sensor calibration, while also allowing a determination of any cross-interference between various solutes in, or properties of, sweat. For example, potassium ($K^+$) and ammonium ($NH_4^+$) are known to interfere with each other in ion-selective electrode sensors. In one embodiment, a calibration module (e.g., module 340) may include a first solution containing a high concentration of $K^+$ and a low concentration of $NH_4^+$. A second solution in the calibration module may contain a low concentration of $K^+$ and a high concentration of $NH_4^+$. Further solutions may contain equal concentrations of $K^+$ and $NH_4^+$, which could be high, moderate, or low. In this manner, any cross-interference between $K^+$ and $NH_4^+$ for a device (e.g., device 300) may be determined.

Figure 4:
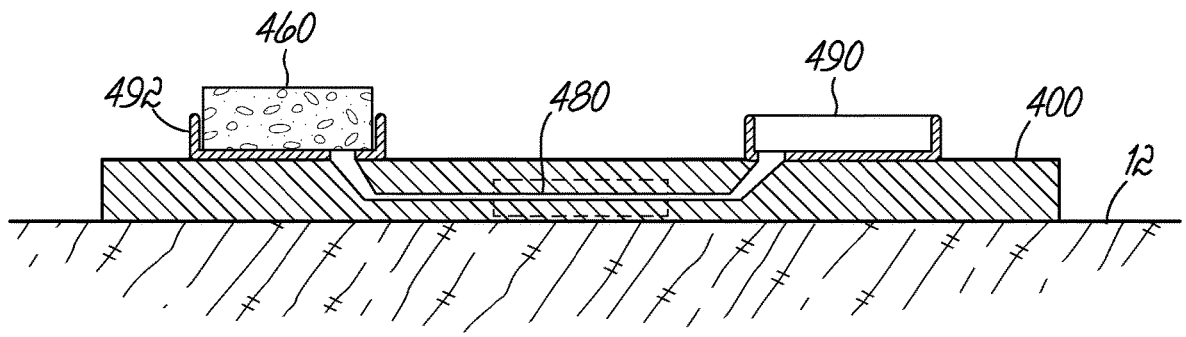
FIG. 4 is a cross-sectional view of a device according to an embodiment of the present invention.

With reference to FIG. 4, device 400 includes an external introduction port 490, a microfluidic component 480 that moves fluid to or past sensors, and an optional outlet port 492 with absorbing sponge 460. Microfluidic component 480 may be, for example, a 50 micron polymer channel that is 500 microns wide. One or more calibration solutions could be introduced at port 490 while the device 400 is on the skin 12. The calibration solution may be introduced at port 490 using a variety of methods. For example, the calibration solution could be introduced at port 490 by the application of droplets, by using a cartridge, by using a carrier, such as those discussed above, or using another approach. In addition to a calibration solution, a fluid that refreshes the usability of sensors may also be introduced to the device 400 though port 490 and be wicked through the microfluidic component 480 across sensors by sponge 460. In various embodiments, the fluid may change the pH level or cause a sensor probe to release an analyte. In one embodiment, such a refreshing fluid could be introduced to the device 400, followed by the introduction of the calibration fluid. The introduction of a fluid (e.g., a calibration solution) may be followed by a removal of the fluid. For example, in one embodiment, the sponge 460 could be removed after collection of the refreshing fluid and disposed of. The sponge 460 could be a wicking sponge material, a textile, hydrogel, or other material capable of wicking and collecting a fluid.

Figure 5:
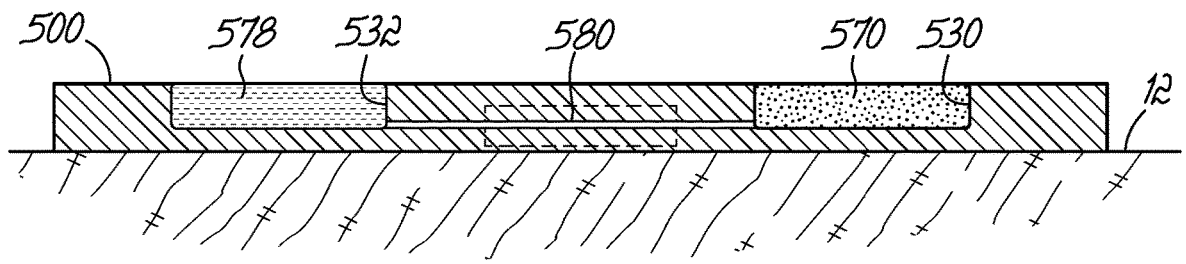
FIG. 5 is a cross-sectional view of a device according to an embodiment of the present invention positioned on skin.

With reference to FIG. 5, a device 500 includes a first reservoir 530 and a second reservoir 532 that are fluidically coupled by microfluidic component 580. The first reservoir 530 includes a calibrating solution 570, and the second reservoir 532 includes a displaceable gas 578. Microfluidic component 580 is designed to provide access to a sensor (not shown). Calibration of the device 500 using aspects of the present invention could occur before device 500 operation begins, before sweat from skin 12 is sampled, or at times during the use of the device 500 using one more methods of timed microfluidic operation known by those skilled in the art. By way of example, the device 500 may include gates that swell (close) or dissolve (open) after prolonged exposure to a fluid. The gates (not shown) may be formed by a swellable polymer or a soluble salt or sugar, for example. The calibration solution 570 could stay in contact with the sensors for a determined period of time before it is removed. The calibration solution 570 may be removed, for example, by wicking or by pumping. Pumping may be accomplished through gas pressure (not shown) using the release of an internal pressurized gas source or generated gas source (e.g., electrolysis of water). Alternatively, the calibration solution 570 could remain in contact with sensors until it is replaced by sweat.

Figure 6A:
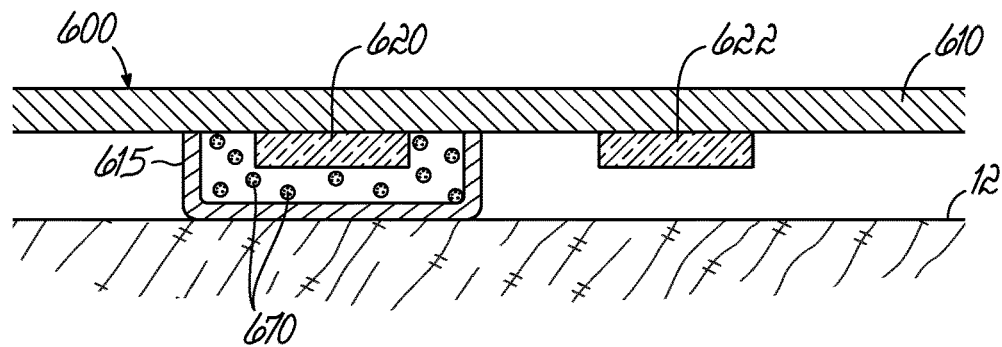
FIG. 6A is a cross-sectional view of a device according to an embodiment of the present invention positioned on skin.
Figure 6B:
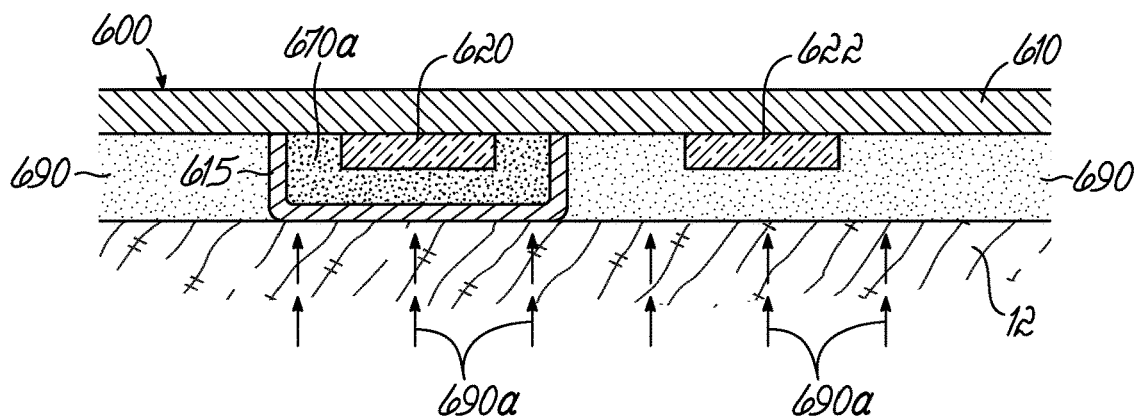
FIG. 6B is a cross-sectional view of the device of FIG. 6A during calibration.

With reference to FIGS. 6A and 6B, a device 600 is shown which includes a substrate 610 carrying two similar sensors 620, 622 and a membrane 615 that covers the sensor 620. The sensors 620, 622 are similar in that, if one is calibrated, they are similar enough that calibration for one can be used for the others. In one embodiment, the sensors are of the same generation type (e.g. amperometric) but have different analyte targets (e.g. glucose and lactate). In another embodiment, the sensors target the same analyte, and calibration for one sensor will typically best predict the calibration for the second. Device 600 further includes a dry dissolvable calibration medium 670 for one or more analytes between the membrane 615 and the sensor 620. The calibration medium 670 could also be a liquid or a gel. FIG. 6B shows a flow of sweat 690 generated by the skin 12 as indicated by arrows 690a. The water in the sweat 690 penetrates through membrane 615 and dissolves calibration medium 670 to create a calibration solution 670a. Membrane 615 allows water transport through the membrane 615, while delaying or preventing transport of analytes to be sensed from the sweat 690 at least during a calibration between sensors. By way of example, the membrane 615 could be made of a dialysis membrane, Nafion membrane, track-etch membrane, reverse-osmosis membrane, or sealed reference electrodes. In this configuration, sensors 620, 622 can be compared in their readings of an analyte. If the concentration of an analyte in solution 670a is known, then the concentration of the analyte in sweat 690 can be better determined through comparison of the measured signal from sensors 620, 622. In an exemplary embodiment, membrane 615 creates a defined volume around sensor 620 such that the concentration of analytes is predictable (i.e., known amount of dilution as the calibration medium 670 dissolves). For example, a porous polymer or polymer textile could be used which has a finite porous volume in it to fix the volume of calibration solution 670a around the sensor 620. In one embodiment, calibration solution 670a may include a concentration of the analyte that is greater than the concentration of that analyte present in sweat. For example, the calibration solution 670a may include an analyte at a concentration roughly 10 times or more than that found in the sweat that wets the calibration medium 670.

Figure 6C:
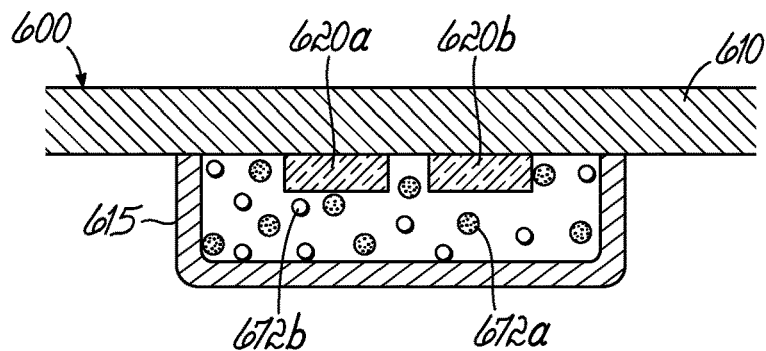
FIG. 6C is a cross-sectional view of a device according to an embodiment of the present invention positioned on skin.

With reference to FIG. 6C, in one embodiment, element 620 of the device 600 represents two or more different sensors 620a and 620b requiring calibration. For example, the first sensor 620a in element 620 could be for detecting cortisol, and often these types of sensors require calibration. Sensor 622 shown in FIG. 6A would, in this example, also be for detecting cortisol and would measure cortisol found in sweat directly. The second sensor 620b in element 620 could be for detecting $Na^+$ (such as an ion-selective electrode or through simple electrical conductance of solution). The dry dissolvable calibration medium 670 includes a known starting concentration of cortisol 672a and $Na^+$ 672b. As water moves through the membrane 615, it dissolves or dilutes the calibration medium 670 to create the calibration solution 270a, in which concentrations of both $Na^+$ and cortisol could be measured. The $Na^+$ sensor 620b may be configured so that it would not need calibration using the calibration solution 270a. For example, sensor 620b may be an ion-selective electrode having a sealed reference electrode (not shown) to allow it to accurately quantify $Na^+$ concentrations. As the $Na^+$ dilutes as the water moves in, the amount of water is also indirectly measured (by measuring $Na^+$), and therefore the amount of dilution of cortisol would be known from the time when the water began moving through the membrane 615 until the water fills the space between the membrane 615 and the sensors 620a, 620b. In summary, the measurement of $Na^+$ would be used to determine the total dilution that has occurred as water moves into the calibrating solution 670a, and therefore the amount of dilution of cortisol in calibrating solution 670a is also known. Therefore a dilution calibration curve could be provided for the first sensor 620a, which would then provide a dilution calibration for sensor 622 as well.

With further reference to FIGS. 6A-6C, in one aspect of the present invention, membrane 615 may act as a binding medium that binds solutes in sweat such that sweat is diluted of one or more analytes before it reaches the calibrating medium. Such a binding medium would be in the sweat flow path between sweat glands and at least one sensor. The binding medium may provide specific binding (e.g., a layer of beads doped with ionophores) or non-specific binding (e.g., cellulose). As a result, the calibration medium 670 would not need to provide a concentration of analyte or analytes greater than that found in real sweat, as the initial sweat which reaches the calibration sensor would be diluted of the analyte to be calibrated. Specific binding materials include beads or other materials those known by those skilled in the art that promote specific absorption.

In another aspect of the present invention, conditions can be provided that denature or alter an analyte in sweat such that its concentration is effectively lowered before reaching a calibration medium. In one embodiment, a binding solute in solution that binds to the analyte in a way similar to how the analyte binds to a probe on the sensor is provided at a location between the sensor and skin. In one embodiment, the binding solute may be present in a wicking textile (not shown) that brings sweat from skin to the sensors. Because the analyte will bind with the binding solute, the sensor probes are prevented from binding with such analytes. For example, the sensor could be an electrochemical aptamer or antibody sensor, and the binding solute could be an aptamer or antibody that is suspended in solution. Those skilled in the art will recognize other techniques that are useful for lowering concentrations of analytes in sweat such that a more pure fluid is provided for the purposes of calibration.

Figure 7A:
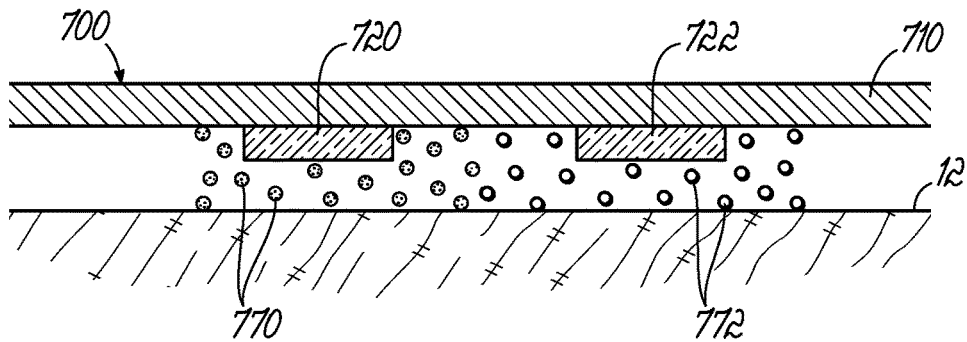
FIG. 7A is a cross-sectional view of a device according to an embodiment of the present invention positioned on skin.
Figure 7B:
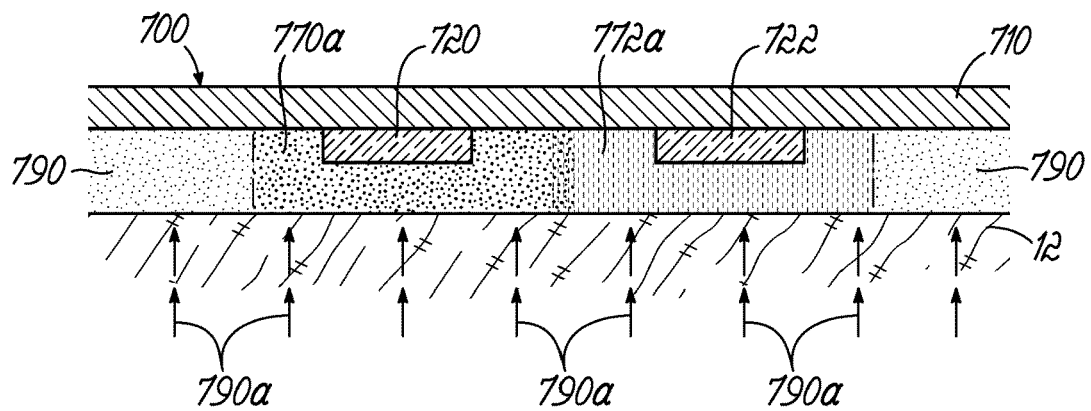
FIG. 7B is a cross-sectional view of the device of FIG. 7A during calibration.
Figure 7C:
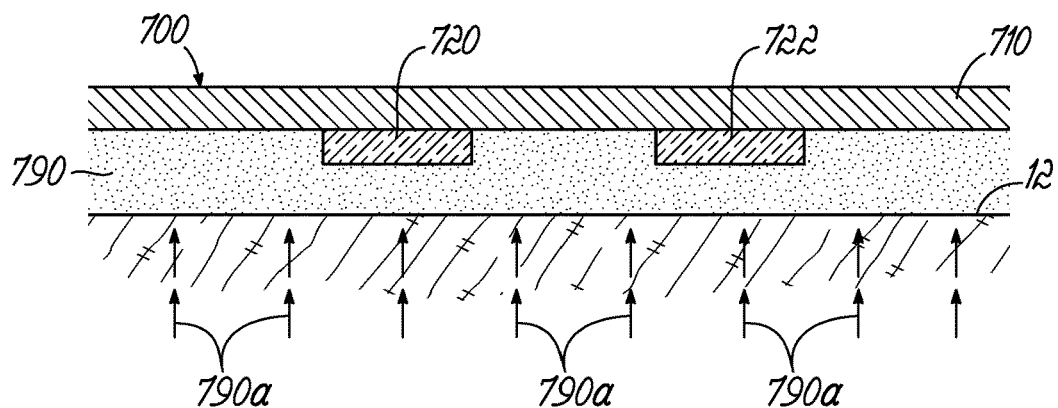
FIG. 7C is a cross-sectional view of the device of FIG. 7A after calibration.

With reference to FIGS. 7A-7C, a device 700 includes a sensor 720 for sensing a first analyte and a sensor 722 for sensing a second analyte, and the device 700 further includes a polymer substrate 710, and calibration mediums 770, 772 for calibrating the first and second sensors 720, 722, respectively. The calibration mediums 770, 772 may be positioned adjacent to the sensors 720, 722 using a variety of techniques. For example, the calibration mediums 770, 772 could be a dry powder placed adjacent to a sensor, held in place by a glue or a dissolvable medium, or held in place by another technique until wetted by sweat. The calibration mediums 770, 772 generally: (1) can rapidly take up sweat and allow wetting of sweat against sensors 720, 722; (2) release a concentration of calibrating analytes into sweat near sensors 720, 722 quickly enough to alter the concentration of said analytes in sweat; (3) maintain calibration concentrations of analytes in sweat long enough for sensor 720, 722 calibration to be performed; and (4) promote a generally fixed fluid volume initially as they uptake sweat such that calibration analyte concentrations are repeatable. In one embodiment, calibration mediums 770, 722 may be made of a material that would rapidly swell to a known volume as it wets but would more slowly dissolve and wash away, therefore allowing adequate time for calibration (discussed further below). With reference to FIG. 7B, once calibration mediums 770, 772 are wetted with sweat 790 generated as shown by arrows 790a, calibration solutions 770a, 772a are formed. Over time, the calibration analytes within calibration solutions 770a, 772a are transported away from sensors 720, 722 by the sweat 790 such that sensing can be performed on new sweat, as shown in FIG. 7C.

Calibration mediums, useful in embodiments of the present invention can be constructed using a variety of methods. With further reference to FIGS. 7A-7C, calibration mediums 770, 772 may release the analytes contained therein initially upon contact with sweat, or at some time thereafter, through time-release techniques. In various embodiments, a calibration medium could be formed from a dissolvable polymer, such as a water soluble polymer or a hydrogel. Exemplary polymers include polyvinylpyrolidone (PVP), polyvinylachohol (PVA), and poly-ethylene oxide. PVP can be used as a dissolvable polymer that can swell with up to 40% water in a humid environment or can be used as a hydrogel if cross-linked using, for example, UV light exposure. Like PVP, PVA can be used as a water dissolvable material or as a hydrogel. Also, such polymers can have a wide range of molecular weights that can affect the rate at which such polymers dissolve. Consider several exemplary embodiments. In one embodiment, a calibration medium of PVP with a known concentration of at least one analyte is coated onto a sensor or is positioned adjacent to a sensor. When wetted or hydrated, the PVP will act as a calibration solution. Such a calibration medium could also contain one or more preservatives. If PVP, or another suitable material, were used as a water dissolvable polymer, its surface would wet quickly with sweat before the PVP appreciably dissolves. Then, before the PVP fully dissolves, the sweat would hydrate the polymer and allow for sensor calibration. Therefore, the polymer itself could provide a predictable volume and dilution of calibrating analytes confined inside the polymer for a period of time (seconds, or minutes) before it fully dissolves. In one embodiment where the device includes a protein-based sensor, such as an electrically active beacon aptamer sensor, the calibrating analyte confined in the polymer could be a protein, such as a cytokine. Initially, as water and ions from sweat permeate the polymer to wet it, the calibrating protein solution would remain at least partially immobilized inside the polymer, and outside proteins in sweat would be at least partially excluded. The calibration medium may be adapted to prevent outside proteins from being absorbed based on the size of the proteins, based on properties such as the solubility or lipophilicity of the proteins. The calibration medium may also include ionophores to allow certain solutes and the water from sweat to electronically activate the sensor while excluding other solutes. Therefore, a predictable dilution or concentration of the calibration medium could be provided long enough to allow sensor calibration (e.g., on the order of seconds or minutes) before the polymer dissolves. In one embodiment, the calibrating analytes may be absorbed by the sensor underneath the polymer, and the sensor will be calibrated when water and salt (i.e., sweat) reaches the sensor, which enables the proper electrical connection needed for a complete sensing circuit. Similarly, hydrogels could be used as calibration mediums as long as a suitable time period for calibration is provided. For example, in one embodiment, the thickness of the hydrogel provides adequate time for the calibrating analyte inside the hydrogel to calibrate the sensor before external analytes in sweat enter the hydrogel and dominate the signal provided from the sensor. It should be recognized that calibration mediums may have alternative configurations. For example, in various embodiments, the calibration medium may be constructed of may be a textile that is coated with analytes or may include multiple layers of polymers or gels having different properties. Additionally, various techniques, such as altering the pH, may be used to remove the calibrating analytes from sensors to prevent interference with measurements of new sweat.

Figure 8:
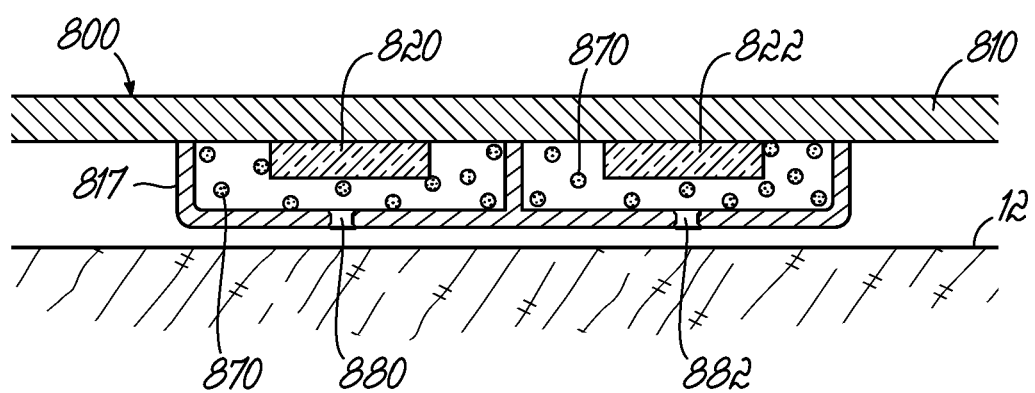
FIG. 8 is a cross-sectional view of a device according to an embodiment of the present invention.

With reference to FIG. 8, a device 800 contains two sensors 820, 822 for example, and two identical calibration mediums 870. Sensors 820, 822 and calibration mediums 870 are enclosed by substrate 810 and seal 817. Seal 817 includes fluidic gates 880, 882. Fluidic gates 880, 882 only allow sweat to reach sensors 820, 822 as determined by the design of the fluidic gates 880, 882 (e.g., based on a dissolution rate of the gate). In one embodiment, when gates 880, 882 allow the passage of fluid, sweat would first enter the space between the membrane 810 and seal 817 and dissolve calibration mediums 870. In this manner, sensors 820, 822 may be calibrated similarly to the calibration methods discussed above. After a period of time (e.g., 30 minutes), the calibration medium 870 would diffuse out through the microfluidic gates 880, 882 as new sweat enters. As the medium 870 diffuses, the analyte concentrations near the sensors 820, 822 would be increasingly dominated by those in new sweat. The device 800 of FIG. 8 is useful when a sensor is to be calibrated and used only when needed. In one embodiment, sensors 820, 822 are one-time use, and the device 800 is configured to perform multiple readings. Where more than one microfluidic gate is used, the gates may be designed to open and close at the same time or at different times. Multiple fluidic gate configurations are possible as known by those skilled in the art, including thermocapillary, electrowetting, melting of wax barriers, or other known techniques. In one embodiment, a wicking element could also be included (not shown) to bring a continuous flow of sweat to the sensor 820 or 822, and mitigate the need for a calibration medium to diffuse out, thereby decreasing the time required to calibrate the device.

With further reference to FIG. 8, in one embodiment, one or both of gates 880, 882 could be a dissolvable polymer (e.g., PVP or PVA) and seal 817 could be a membrane (e.g., a dialysis membrane) that is permeable to water but highly impermeable to at least one analyte to be calibrated. Therefore, as sweat wets the membrane 817, water moves though the membrane 817 and dissolves calibration medium 870 and creates a calibrating solution for calibrating at least one of the sensors 820, 822. Later, as at least one of the gates 880, 882 dissolves away, sweat including the analytes that were previously excluded by membrane 817 enters through the dissolved gate 880, 882 and begins to be sensed by the now-calibrated sensor 820 or sensor 822. The exact dimensions shown in FIG. 8 are non-limiting and are provided as an example only. For example, in one embodiment, gates 880, 882 could have larger area than membrane 817.

For purpose of clarity, layers and materials in the above-described embodiments of the present invention are illustrated and described as being positioned 'between' sweat and sensors and, in some cases, 'between' one or more of each layer or material. However, terms such as 'between' should not be so narrowly interpreted. The term 'between' may also be interpreted to mean 'in the fluidic pathway of interest'. For example, in one embodiment, a microfluidic channel that is 3 mm long and 300 µm×100 µm in area could be positioned in the pathway (or 'between') of flow of sweat from the skin to the sensors and may include any one or more of the features illustrated and discussed for the present invention. Therefore, 'between' or other terms should be interpreted within the spirit of the present invention, and alternate embodiments, although not specifically illustrated or described, are included with the present invention so long as they would obviously capture similar purpose or function of the illustrated embodiments.

This has been a description of the present invention along with a preferred method of practicing the present invention, however the invention itself should only be defined by the appended claims.

What is claimed is:

1. A self-calibrating sweat sensor device comprising:
   a sweat sensor module that includes a sensor, the sweat sensor module having a surface adapted to contact skin of a subject during subject sweat sensing; and
   a calibration module removably affixed to the surface of the sweat sensor module that is adapted to contact skin of the subject during subject sweat sensing, the calibration module having a housing that forms a reservoir and defines an aperture, the aperture being adjacent the sensor in the sensor module when the calibration module is removably affixed to said surface, the reservoir having a first portion separated from a second portion by a rupturable membrane, wherein the rupturable membrane is initially in a non-ruptured state when the calibration module is removably affixed to the sweat sensor module, wherein said surface of the sweat sensing module remains external to the calibration module in the non-ruptured state and in a ruptured state of the rupturable membrane, and wherein the first portion in communication with the aperture and the second portion including at least one calibration medium.

2. The device of claim 1, wherein the second portion of the reservoir is collapsible.

3. The device of claim 1, further comprising a sponge in the first portion of the reservoir.

4. The device of claim 1, further comprising a flow restrictor that restricts a flow of sweat or calibration medium to the sensor.

5. The device of claim 4, wherein the flow restrictor is between the sweat sensor module and the calibration module.

6. The device of claim 4, wherein the flow restrictor is selected from a flow limiting element, a flow constriction element, and a flow stopping element.

7. The device of claim 6, wherein the flow limiting element is a textile and the flow constriction element is a small aperture in a film.

8. The device of claim 1, wherein the second portion includes more than one calibration medium.

9. The device of claim 8, wherein the second portion is divided into a plurality of subchambers and each subchamber includes a different calibration medium.

* * * * *